United States Patent

Heinemann et al.

[11] Patent Number: 5,728,737
[45] Date of Patent: Mar. 17, 1998

[54] N-ALKOXY-AMIDINE DERIVATIVES

[75] Inventors: Ulrich Heinemann, Leichlingen; Bernd-Wieland Krüger, Bergisch Gladbach; Ralf Tiemann, Leverkusen; Stefan Dutzmann, Hilden; Klaus Stenzel, Düsseldorf, all of Germany

[73] Assignee: Bayer Aktiengesellschaft, Leverkusen, Germany

[21] Appl. No.: 776,225

[22] PCT Filed: Jul. 17, 1995

[86] PCT No.: PCT/EP95/02797

§ 371 Date: Jan. 23, 1997

§ 102(e) Date: Jan. 23, 1997

[87] PCT Pub. No.: WO96/04239

PCT Pub. Date: Feb. 15, 1996

[30] Foreign Application Priority Data

Jul. 29, 1994 [DE] Germany .................. 44 26 940.4

[51] Int. Cl.⁶ .................. A01N 37/18; A01N 43/54; A01N 43/82; A01N 37/52; C07C 233/64; C07C 257/18; C07D 239/02; C07D 285/08

[52] U.S. Cl. .................. 514/619; 514/618; 514/620; 514/622; 514/636; 514/637; 514/633; 514/361; 514/269; 514/256; 564/162; 564/163; 564/164; 564/170; 564/171; 564/172; 564/175; 564/180; 564/226; 564/229; 564/243; 564/246; 544/319; 544/326; 544/335; 544/242; 548/128; 548/129; 548/130

[58] Field of Search .................. 564/164, 163, 564/162, 169, 165, 170, 180, 171, 175, 246, 226, 229, 243; 514/617, 618, 619, 620, 621, 622, 637, 636, 633, 269, 256, 361; 544/319, 326, 335, 242; 548/128, 129, 130

[56] References Cited

U.S. PATENT DOCUMENTS

| 5,194,662 | 3/1993 | Brand et al. | 560/35 |
| 5,534,550 | 7/1996 | Gerdes et al. | 514/620 |
| 5,556,884 | 9/1996 | Oberdorf et al. | 514/620 |

OTHER PUBLICATIONS

Trah et al, "Preparation of Pesticidal Tris–Oximino Heterocyclic Compounds", CA126: 157524, (1997).

*Primary Examiner*—Deborah Lambkin
*Attorney, Agent, or Firm*—Sprung Kramer Schaeffer & Briscoe

[57] ABSTRACT

The present invention relates to novel N-alkoxy-amidine derivatives of the formula (I), to a process for their preparation and to their use as pesticides. In addition, the invention also relates to novel intermediates and to a process for their preparation.

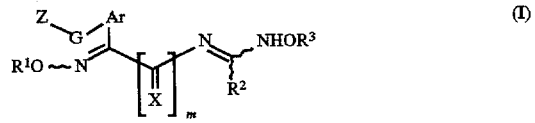

10 Claims, No Drawings

N-ALKOXY-AMIDINE DERIVATIVES

This application is a 371 of PCT/EP45/0279 Jul. 17, 1995.

The present invention relates to novel N-alkoxy-amidine derivatives, to a process for their preparation and to their use as pesticides. In addition, the invention also relates to novel intermediates and to a process for their preparation.

It is known that different substituted alkoxyimino- and alkoxymethyleneacetamides possess fungicidal properties (cf., e.g., EP-A 398 692, EP-A 468 775, DE-A 40 30 038 and WO-A 92/13 830).

However, in particular at low rates of application and concentrations, the activity of these previously known compounds is not completely satisfactory in all areas of use.

Novel N-alkoxy-⊕amidine derivatives of the general formula (I)

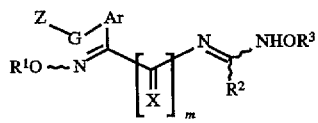

in which

Ar represents in each case optionally substituted arylene or heteroarylene;

G represents a single bond for oxygen, represents alkanediyl, alkenediyl, oxaalkenediyl or alkinediyl which are in each case optionally substituted by halogen, hydroxyl, alkyl, halogenoalkyl or cycloalkyl, or represents one of the following groupings —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —CQ—CH$_2$— or —N=N—C(R$^4$)=N—O—, where n represents the numbers 0, 1 or 2, Q represents oxygen or sulphur, R$^1$ represents hydrogen or alkyl;

R$^2$ represents hydrogen or alkyl;

R$^3$ represents hydrogen or alkyl;

R$^4$ represents hydrogen, cyano or in each case optionally substituted alkyl, alkoxy, alkylthio, alkylamino, dialkylamino or cycloalkyl, and R$^5$ represents hydrogen, hydroxyl, cyano or in each case optionally substituted alkyl, alkoxy or cycloalkyl;

X represents oxygen or sulphur;

m represents the numbers 0 or 1, and

Z represents in each case optionally substituted alkyl, alkenyl, alkinyl, cycloalkyl, aryl or heterocyclyl, have now been found.

It has furthermore been found that the novel N-alkoxy-amidine derivatives of the general formula (I) are obtained when N-N-dialkyl-amidine derivatives of the formula (II)

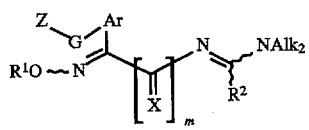

in which

Ar, G, R$^1$, R$^2$, X, Z and m have the abovementioned meaning, and

Alk represents alkyl, are reacted with hydroxylamine derivatives of the general formula (III)

$$H_2N-O-R^3 \quad (III)$$

in which

R$^3$ has the abovementioned meaning, or with their acid-addition salts in the presence of a diluent and, where appropriate, in the presence of a reaction auxiliary.

Finally, it has been found that the novel N-alkoxy-amidine derivatives of the general formula (I) exhibit a powerful fungicidal activity.

The novel compounds can, where appropriate, be present as mixtures of different possible isomeric forms, in particular E isomers and Z isomers. Both the E isomers and the Z isomers, and also arbitrary mixtures of these isomers, are claimed.

The invention preferably relates to compounds of the formula (I) in which

Ar represents in each case optionally substituted phenylene or naphthylene, or represents heteroarylene having 5 or 6 ring members of which at least one represents oxygen, sulphur or nitrogen and, where appropriate, one or two further members represent nitrogen, with the possible substituents preferably being selected from the following list:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case from 1 to 6 carbon atoms, in each case straight-chain or branched alkenyl, alkenyloxy or alkinyloxy having in each case from 2 to 6 carbon atoms, in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms, in each case straight-chain or branched halogenoalkenyl or halogenoalkenyloxy having in each case from 2 to 6 carbon atoms and from 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties, or in each case doubly linked alkylene or dioxyalkylene which in each case have from 1 to 6 carbon atoms and which are in each case optionally substituted identically or differently, once or more than once, by halogen and/or straight-chain or branched alkyl having from 1 to 4 carbon atoms and/or straight-chain or branched halogenoalkyl having from 1 to 4 carbon atoms and from 1 to 9 identical or different halogen atoms, G represents a single bond, represents oxygen, represents alkanediyl, alkenediyl, oxaalkenediyl or alkinediyl which in each case have up to 4 carbon atoms and which are in each case optionally substituted by halogen, hydroxyl, $C_1$–$C_4$-alkyl, $C_1$–$C_4$-halogenoalkyl or $C_3$–$C_6$-cycloalkyl, or represents one of the following groupings —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N═N—, —S(O)$_n$—, —CH$_2$—S(O)$_n$—, —CQ—, —S(O)$_n$—CH$_2$—, —C(R$^4$)═N—O—, —C(R$^4$)═N—O—CH$_2$—, —N(R$^5$)—, —CQ—N(R$^5$)—, —N(R$^5$)—CQ—, —Q—CQ—N(R$^5$)—, —N═C(R$^4$)—Q—CH$_2$—, —CH$_2$—O—N═C(R$^4$)—, —N(R$^5$)—CQ—Q—, —CQ—N(R$^5$)—CQ—Q—, —N(R$^5$)—CQ—Q—CH$_2$—, —CQ—CH$_2$— or —N═N—C(R$^4$)═N——, where n represents the numbers 0, 1 or 2, Q represents oxygen or sulphur, R$^4$ represents hydrogen or cyano, represents alkyl, alkoxy, alkylthio, alkylamino or dialkylamino which in each case have from 1 to 6 carbon atoms in the alkyl groups and which are optionally substituted by halogen, cyano or $C_1$–$C_4$-alkoxy, or represents cycloalkyl which has from 3 to 6 carbon atoms and which is in each case optionally substituted by halogen, cyano, carboxyl, $C_1$–$C_4$-alkyl or $C_1$–$C_4$-alkoxy-carbonyl, and R$^5$ represents hydrogen, hydroxyl or cyano, or represents alkyl which has from 1 to 6 carbon atoms and which is optionally substituted by halogen, cyano or $C_1$–$C_4$-alkoxy, or represents cycloalkyl which has from 3 to 6 carbon atoms and which is optionally substituted by halogen, cyano, carboxyl, $C_1$–$C_4$-alkyl or $C_1$–$C_4$-alkoxy-carbonyl.

R$^1$ represents hydrogen or straight-chain or branched alkyl having from 1 to 4 carbon atoms.

R$^2$ represents hydrogen or straight-chain or branched alkyl having from 1 to 4 carbon atoms.

R$^3$ represents hydrogen or straight-chain or branched alkyl having from 1 to 4 carbon atoms.

X represents oxygen or sulphur.

m represents the numbers 0 or 1, and

Z represents alkyl which has from 1 to 8 carbon atoms and which is optionally substituted by halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by halogen), represents alkenyl or alkinyl which in each case have up to 8 carbon atoms and which are in each case optionally substituted by halogen, represents cycloalkyl which has from 3 to 6 carbon atoms and which is in each case optionally substituted by halogen, cyano, carboxyl, phenyl (which is optionally substituted by halogen cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represents in each case optionally substituted phenyl, naphthyl or (optionally benzofuzed) heterocyclyl having 5 or 6 ring members of which at least one represents oxygen, sulphur or nitrogen and, where appropriate, one or two further members represent nitrogen, with the possible substituents preferably being selected from the following list:

oxygen (as a replacement for two geminate hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case from 1 to 6 carbon atoms, in each case straight-chain or branched alkenyl or alkenyloxy having in each case from 2 to 6 carbon atoms, in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms, in each case straight-chain or branched halogenoalkenyl or halogenoalkenyloxy having in each from 2 to 6 carbon atoms and from 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties, in each case doubly linked alkylene or dioxyalkylene which in each case have from 1 to 6 carbon atoms and which are in each case optionally substituted identically or differently, once or more than once, by halogen and/or straight-chain or branched alkyl having from 1 to 4 carbon atoms and/or straight-chain or branched halogenoalkyl having from 1 to 4 carbon atoms and from 1 to 9 identical or different halogen atoms, cycloalkyl having from 3 to 6 carbon atoms, heterocyclyl or heterocyclyl-methyl having in each case from 3 to 7 ring members of which in each case from 1 to 3 are identical or different heteroatoms, in particular nitrogen, oxygen and/or sulphur, and also phenyl, phenoxy, benzyl, benzyloxy, phenylethyl or phenylethyloxy which are in each case optionally substituted identically or differently, once or more than once, in the phenyl moiety by halogen cyano, nitro, carboxyl, carbamoyl and/or straight-chain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxy having from 1 to 4 carbon atoms and from 1 to 9 identical or different halogen atoms and/or alkylcarbonyl or alkoxycarbonyl having in each case up to 5 carbon atoms.

In the definitions, the saturated or unsaturated hydrocarbon chains, such as alkyl, alkanediyl, alkenyl or alkinyl, are in each case straight-chain or branched, including when they are linked to heteroatoms, as in alkoxy, alkylthio or alkylamino.

In general, halogen represents fluorine, chlorine, bromine or iodine, preferably fluorine, chlorine or bromine, and in particular fluorine or chlorine.

The invention relates, in particular, to compounds of the formula (I) in which

Ar represents in each case optionally substituted ortho-, meta- or para-phenylene, represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, with the possible substituents being selected, in particular, from the following list:

fluorine, chlorine, cyano, methyl, ethyl, trifluoromethyl, methoxy, ethoxy, methylthio, methylsulphinyl or methylsulphonyl.

G represents a single bond, represents oxygen, represents methylene, dimethylene (ethane-1,2-diyl), ethene-1,2-diyl or ethine-1,2-diyl, which are in each case optionally substituted by fluorine, chlorine, hydroxyl, methyl, ethyl, n- or i-propyl, trifluoromethyl, cyclopropyl, cyclobutyl, cyclopentyl or cyclohexyl, or represents one of the following groupings
—Q—CQ—,  —CQ—Q—,  —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q— or —N(R$^5$)—CQ—Q—CH$_2$—, where n represents the numbers 0, 1 or 2, Q represents oxygen or sulphur, R$^4$ represents hydrogen or cyano, or represents methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino which are optionally substituted by fluorine, chlorine, cyano, methoxy or ethoxy, or represents cyclopropyl, cyclobutyl, cyclopentyl or cyclohexyl which are in each case optionally substituted by fluorine, chlorine, cyano, carboxyl, methyl, ethyl, n- or i-propyl, methoxycarbonyl or ethoxy-carbonyl, and R$^5$ represents hydrogen, hydroxyl or cyano, or represents methyl, ethyl, n- or i-propyl, n-, i-, s- or t-butyl which are in each case optionally substituted by fluorine, chlorine, cyano, methoxy or ethoxy, or represents cyclopropyl, cyclobutyl, cyclopentyl or cyclohexyl which are in each case optionally substituted by fluorine, chlorine, cyano, carboxyl, methyl, ethyl, n- or i-propyl, methoxycarbonyl or ethoxycarbonyl.

R$^1$ hydrogen, methyl, ethyl, no or i-propyl and also n-, i-, s- or t-butyl.

R$^2$ represents hydrogen, methyl, ethyl, n- or i-propyl and also n-, i-, so or t-butyl.

R$^3$ represents hydrogen, methyl, ethyl, n- or i-propyl and also n-, i-, s- or t-butyl.

X represents oxygen or sulphur.

m represents the numbers 0 or 1, and

Z represents methyl, ethyl, n- or i-propyl, n-, i-, so or t-butyl which are optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (which are in each case optionally substituted by fluorine and/or chlorine), represents allyl, crotonyl, 1-methyl-allyl, propargyl or 1-methyl-propargyl which are in each case optionally substituted by fluorine, chlorine or bromine, represents cyclopropyl, cyclobutyl, cyclopentyl or cyclohexyl which are in each case optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzthiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, with the possible substituents preferably being selected from the following list:

oxygen (as a replacement for two geminate hydrogen atoms), fluorine, chlorine, bromine, cyano, nitro, amino, hydroxyl, formyl, carboxyl, carbamoyl, thiocarbamoyl, methyl, ethyl, n- or i-propyl, no, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl; trimethylene (propane-1,3-diyl), methylenedioxy or ethylenedioxy, cyclopropyl, cyclobutyl, cyclopentyl or cyclohexyl which are in each case optionally substituted identically or differently, once or more than once, by fluorine, chlorine, methyl, ethyl, n- or i-propyl, and also phenyl, phenoxy, benzyl or benzyloxy which are in each case optionally substituted identically or differently, once or more than once, in the phenyl moiety by fluorine, chlorine, bromine, cyano, nitro, carboxyl, carbamoyl, methyl, ethyl, n- or i-propyl, n-, i-, s- or t-butyl, trifluoromethyl, methoxy, ethoxy, n- or i-propoxy, difluoromethoxy, trifluoromethoxy, acetyl, methoxycarbonyl or ethoxycarbonyl.

A particularly preferred group of novel compounds are those compounds of the formula (I) in which Ar represents ortho-phenylene, pyridine-2,3-diyl or thiophene-2,3-diyl, G represents oxygen, methylene or one of the following groupings
—CH$_2$—O—, —O—CH$_2$—, —S(O)$_n$—, —CH$_2$—S(O)$_n$—, —S(O)$_n$—CH$_2$—, —C(R$^4$)=N—O—, —O—N=C(R$^4$)—, —C(R$^4$)=N—O—CH$_2$—, —N(R$^5$)— or —CH$_2$—O—N=C(R$^4$)—, where n represents the numbers 0, 1 or 2, R$^4$ represents hydrogen, methyl or ethyl, and R$^5$ represents hydrogen, methyl or ethyl.

R$^1$ represents methyl.

R$^2$ represents hydrogen or methyl.

R$^3$ represents hydrogen or methyl.

X represents oxygen.

m represents the numbers 0 or 1, and

Z represents in each case optionally substituted phenyl, pyridinyl, pyrimidinyl, pyridazinyl, pyrazinyl, 1,2,3-triazinyl, 1,2,4-triazinyl or 1,3,5-triazinyl, with the possible substituents preferably being selected from the following list:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoxyiminomethyl, ethoxyiminomethyl, methoxyiminoethyl, ethoxyiminoethyl, methylenedioxy or ethylenedioxy which are in each case optionally substituted identically or differently, once or more than once, by fluorine, chlorine, methyl or ethyl, and also phenyl, phenoxy, benzyl or benzyloxy which are in each case optionally substituted identically or differently, once or more than once, in the phenyl moiety by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

The above listed general radical definitions or those given in preference ranges apply both to the end products of the formula (I) and also, in a corresponding manner, to the starting compounds or intermediates which are in each case required for the preparation.

These radical definitions can be combined arbitrarily, that is also between the given ranges of preferred compounds.

Examples of the novel compounds are listed in Tables 1 to 60:

TABLE 1

TABLE 2
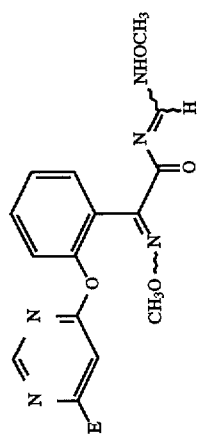
(IB)
where E represents the following substituents:

TABLE 2-continued where E represents the following substituents:

TABLE 3
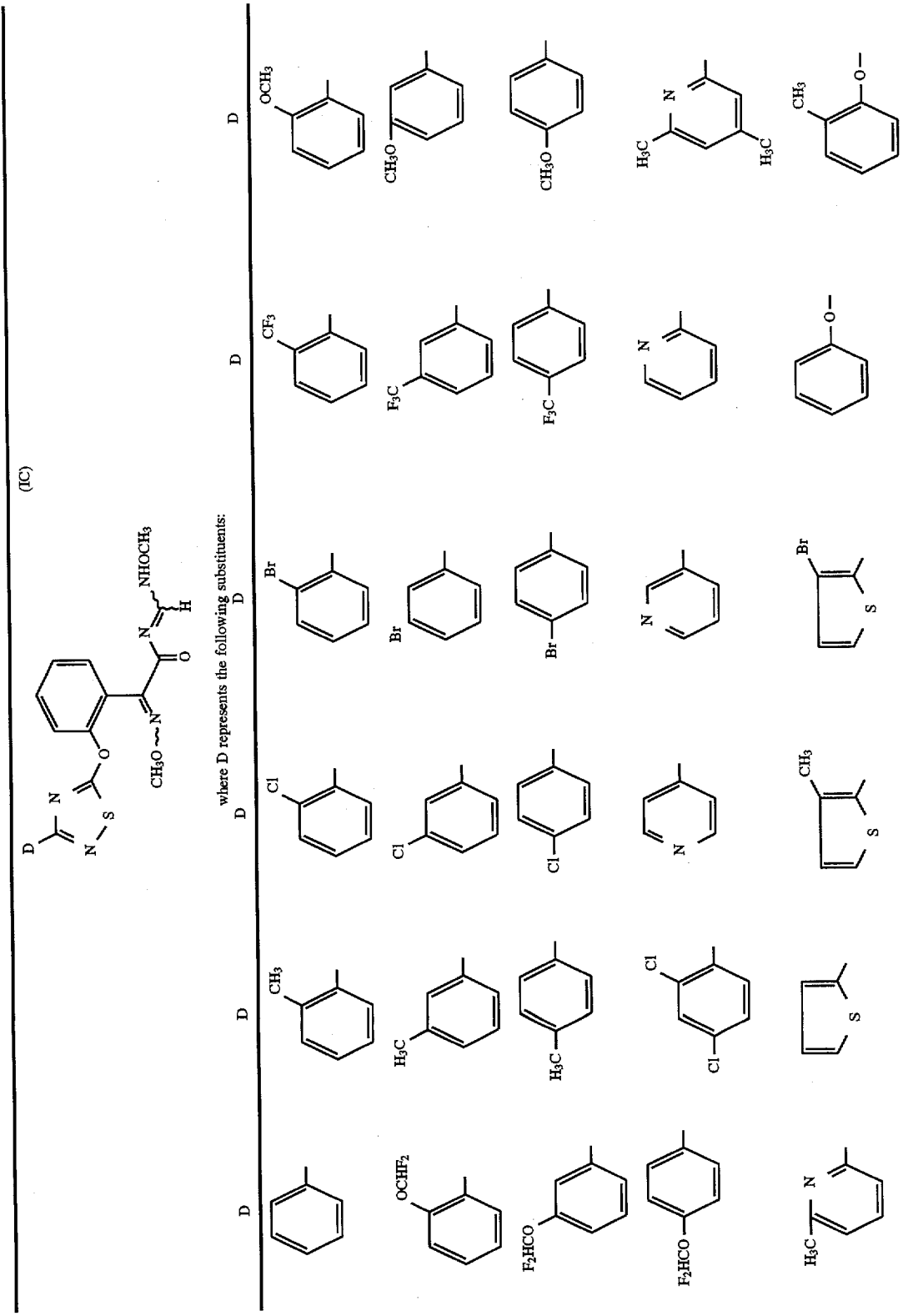

TABLE 3-continued

Structure (IC):

A benzene ring bearing two ortho substituents:
- An O-C(=N-S-)-N=CH-D group (1,3,4-thiadiazole-like) where the ring carbon is attached to D
- A -C(=NOCH₃)-C(=O)-NHOCH₃ group where D represents the following substituents:

| D | D | D | D | D | D |
|---|---|---|---|---|---|
| 2-Cl-C₆H₄-O- | 4-CN-C₆H₄-O- (CN at 2-position) | 4-CH₃-C₆H₄-O- (H₃C-) | 4-Cl-C₆H₄-O- | 4-Br-C₆H₄-O- | C₆H₅-S- |
| 2-CH₃-C₆H₄-S- | 2-Cl-C₆H₄-S- | C₆H₅-CH₂- | 2-Cl-C₆H₄-CH₂- | 2-CH₃-C₆H₄-CH₂- (CH₃) | 4-Br-C₆H₄-CH₂- |
| C₆H₅-CH₂-S- | 2-Cl-C₆H₄-CH₂-S- | 2-CH₃-C₆H₄-CH₂-S- (CH₃) | 4-Cl-C₆H₄-CH₂-S- | 4-CH₃-C₆H₄-CH₂-S- (H₃C) | 2,4-Cl₂-C₆H₃-CH₂-S- |

TABLE 4

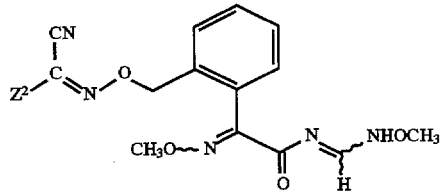

(ID)

where $Z^2$ represents the following substituents:

| $Z^2$ | $Z^2$ | $Z^2$ | $Z^2$ | $Z^2$ | $Z^2$ |
|---|---|---|---|---|---|
| phenyl | 2-Cl-phenyl | 2-CH₃-phenyl | 3-Cl-phenyl | 3-Br-phenyl | 3-CH₃-phenyl |
| 3-CF₃-phenyl | 4-Cl-phenyl | 4-F-phenyl | 4-CH₃-phenyl | 4-NO₂-phenyl | 2,3-Cl₂-phenyl |
| 2,6-Cl₂-phenyl | 3,4-(OCH₃)₂-phenyl | 4-pyridyl | 3-pyridyl | 3-SF₅-phenyl | |

TABLE 5

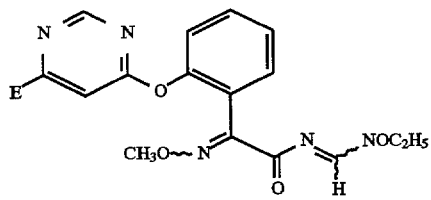

(IE)

where $Z^2$ represents the substituents specified in Table 4.

TABLE 6

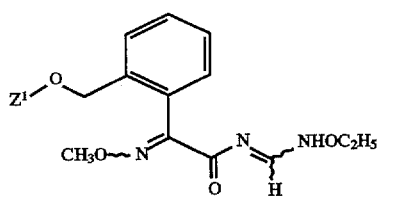

(IA-1)

where $Z^1$ represents the radicals specified in Table 1.

TABLE 7

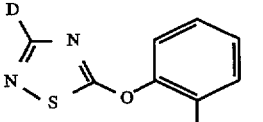

(IB-1)

where E represents the substituents specified in Table 2.

TABLE 8

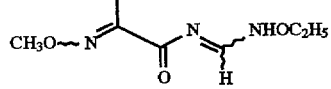

(IC-1)

where D represents the substituents specified in Table 3.

where D represents the substituents specified in Table 3.

TABLE 9

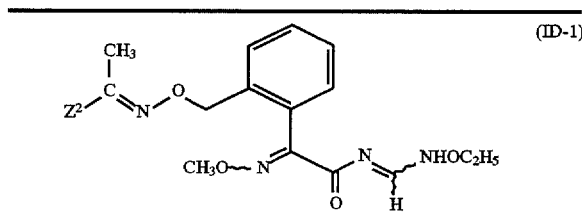
(ID-1)

where $Z^2$ represents the substituents specified in Table 4.

TABLE 10

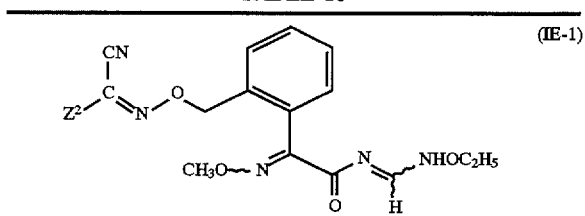
(IE-1)

where $Z^2$ represents the substituents specified in Table 4.

TABLE 11

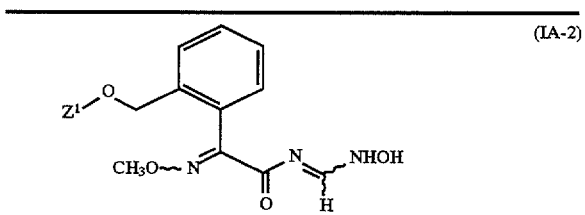
(IA-2)

where $Z^1$ represents the radicals specified in Table 1.

TABLE 12

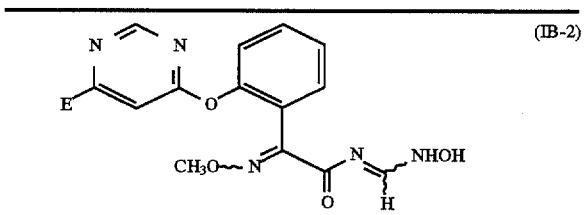
(IB-2)

where E represents the substituents specified in Table 2.

TABLE 13

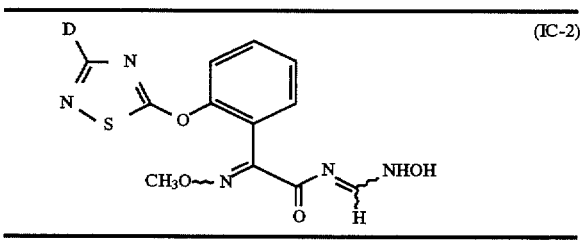
(IC-2)

TABLE 14

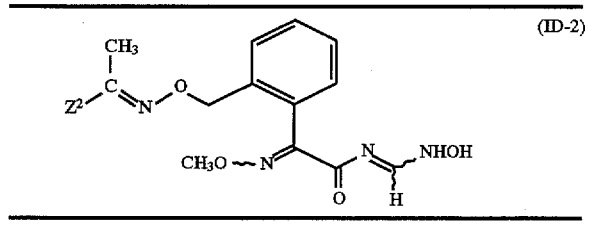
(ID-2)

where $Z^2$ represents the substituents specified in Table 4.

TABLE 15

(IE-2)

where $Z^2$ represents the substituents specified in Table 4.

TABLE 16

(IA-3)

where $Z^1$ represents the radicals specified in Table 1.

TABLE 17

(IB-3)

where E represents the substituents specified in Table 2.

TABLE 18

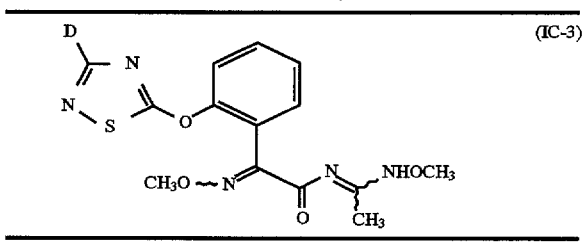
(IC-3)

where D represents the substituents specified in Table 3.

TABLE 19

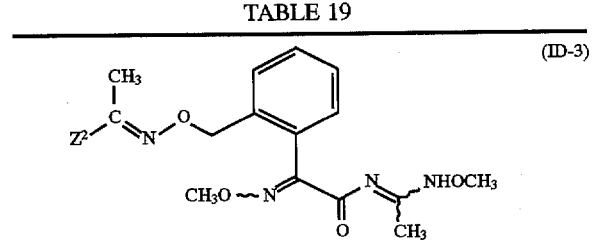

(ID-3)

where $Z^2$ represents the substituents specified in Table 4.

TABLE 20

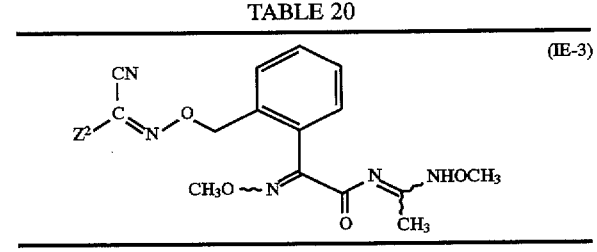

(IE-3)

where $Z^2$ represents the substituents specified in Table 4.

TABLE 21

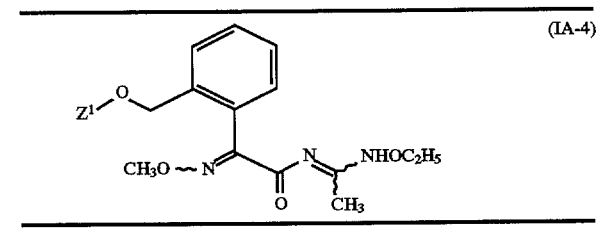

(IA-4)

where $Z^1$ represents the radicals specified in Table 1.

TABLE 22

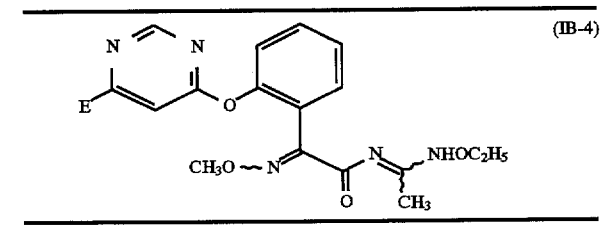

(IB-4)

where E represents the substituents specified in Table 2.

TABLE 23

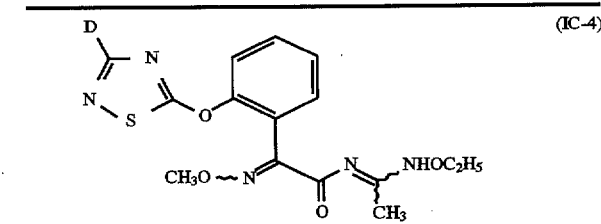

(IC-4)

where D represents the substituents specified in Table 3.

TABLE 24

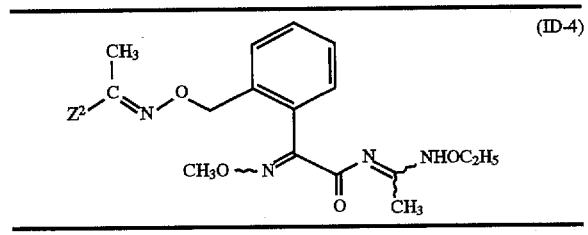

(ID-4)

where $Z^2$ represents the substituents specified in Table 4.

TABLE 25

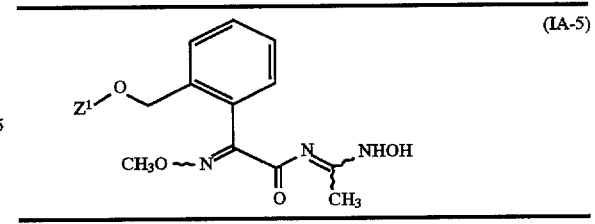

(IE-4)

where $Z^2$ represents the substituents specified in Table 4.

TABLE 26

(IA-5)

where $Z^1$ represents the radicals specified in Table 1.

TABLE 27

(IB-5)

where E represents the substituents specified in Table 2.

TABLE 28

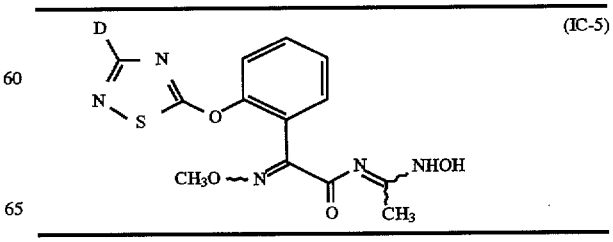

(IC-5)

where D represents the substituents specified in Table 3.

TABLE 29

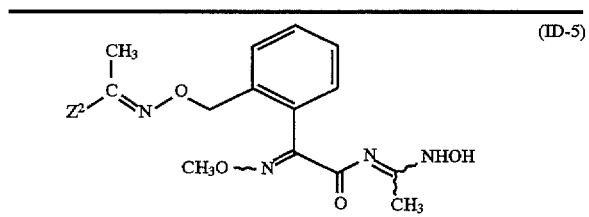
(ID-5)

where $Z^2$ represents the substituents specified in Table 4.

TABLE 30

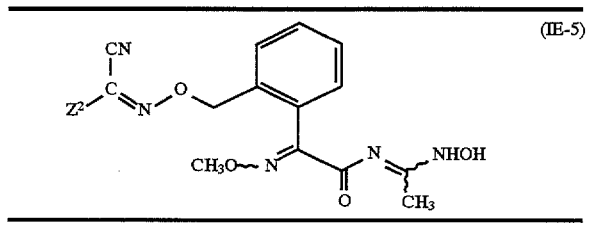
(IE-5)

where $Z^2$ represents the substituents specified in Table 4.

TABLE 31

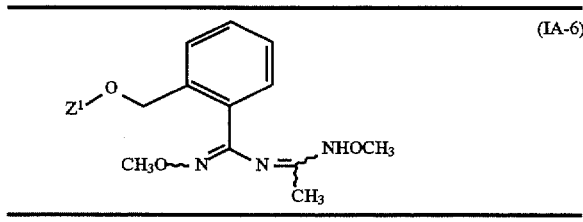
(IA-6)

where $Z^1$ represents the radicals specified in Table 1.

TABLE 32

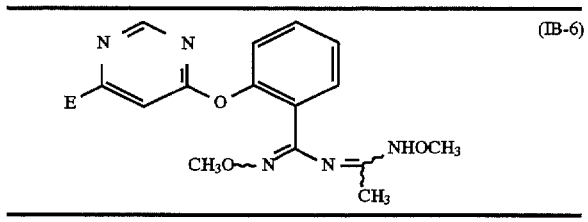
(IB-6)

where E represents the substituents specified in Table 2.

TABLE 33

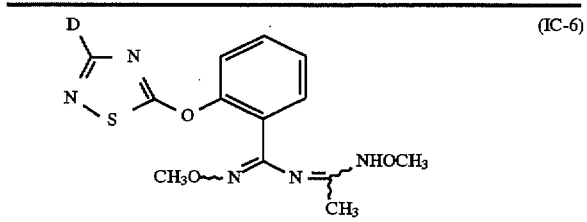
(IC-6)

where D represents the substituents specified in Table 3.

TABLE 34

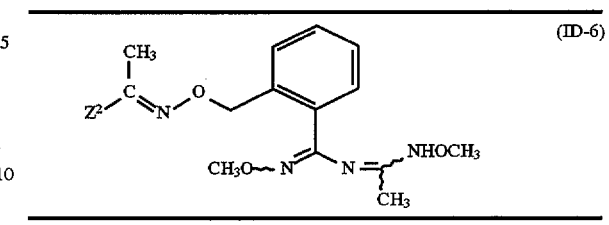
(ID-6)

where $Z^2$ represents the substituents specified in Table 4.

TABLE 35

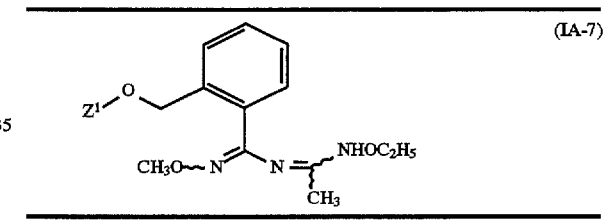
(IE-6)

where $Z^2$ represents the substituents specified in Table 4.

TABLE 36

(IA-7)

where $Z^1$ represents the radicals specified in Table 1.

TABLE 37

(IB-7)

where E represents the substituents specified in Table 2.

TABLE 38

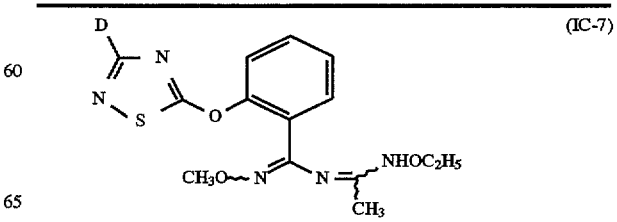
(IC-7)

TABLE 39

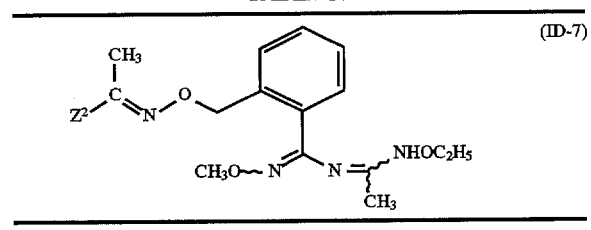
(ID-7)

where $Z^2$ represents the substituents specified in Table 4.

TABLE 40

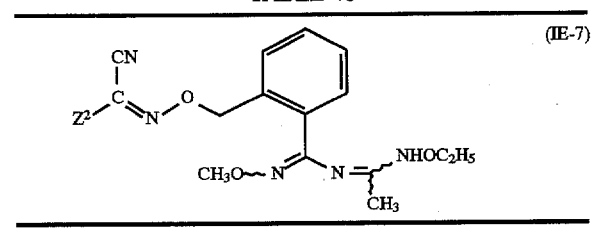
(IE-7)

where $Z^2$ represents the substituents specified in Table 4.

TABLE 41

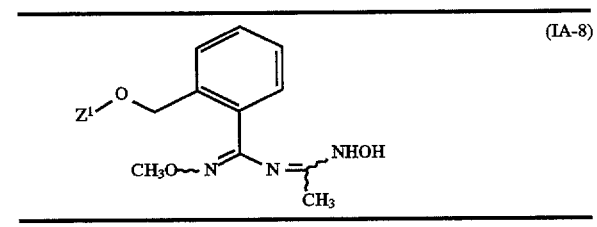
(IA-8)

where $Z^1$ represents the radicals specified in Table 1.

TABLE 42

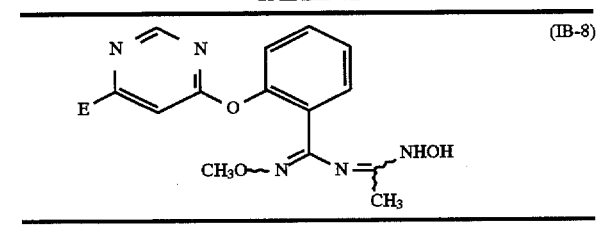
(IB-8)

where E represents the substituents specified in Table 2.

TABLE 43

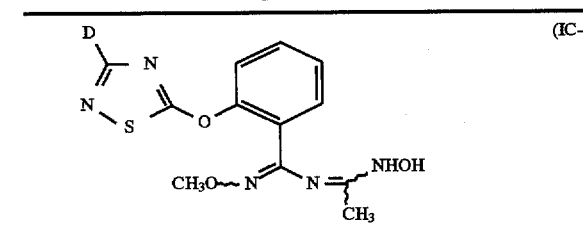
(IC-8)

where D represents the substituents specified in Table 3.

TABLE 44

(ID-8)

where $Z^2$ represents the substituents specified in Table 4.

TABLE 45

(IE-8)

where $Z^2$ represents the substituents specified in Table 4.

TABLE 46

(IA-9)

where $Z^1$ represents the radicals specified in Table 1.

TABLE 47

(IB-9)

where E represents the substituents specified in Table 2.

TABLE 48

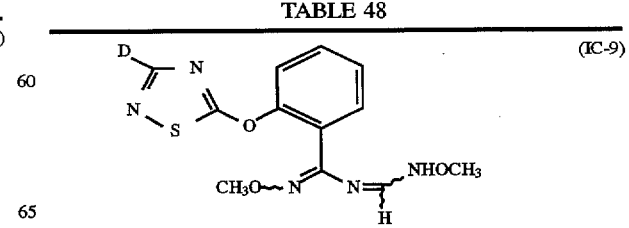
(IC-9)

where D represents the substituents specified in Table 3.

TABLE 49

(ID-9)

[Chemical structure showing compound with CH₃, Z², N, O, CH₃O—N, NHOCH₃, H substituents on benzene ring]

where Z² represents the substituents specified in Table 4.

TABLE 50

(IE-9)

[Chemical structure showing compound with CN, Z², N, O, CH₃O—N, NHOCH₃, H substituents on benzene ring]

where Z² represents the substituents specified in Table 4.

TABLE 51

(IA-10)

[Chemical structure showing compound with Z¹, O, CH₃O—N, NHOC₂H₅, H substituents on benzene ring]

where Z¹ represents the radicals specified in Table 1.

TABLE 52

(IB-10)

[Chemical structure showing pyrimidine compound with E, CH₃O—N, NHOC₂H₅, H substituents]

where E represents the substituents specified in Table 2.

TABLE 53

(IC-10)

[Chemical structure showing thiadiazole compound with D, N, S, O, CH₃O—N, NHOC₂H₅, H substituents]

where D represents the substituents specified in Table 3.

TABLE 54

(ID-10)

[Chemical structure showing compound with CH₃, Z², N, O, CH₃O—N, NHOC₂H₅, H substituents on benzene ring]

where Z² represents the substituents specified in Table 4.

TABLE 55

(IE-10)

[Chemical structure showing compound with CN, Z², N, O, CH₃O—N, NHOC₂H₅, H substituents on benzene ring]

where Z² represents the substituents specified in Table 4.

TABLE 56

(IA-11)

[Chemical structure showing compound with Z¹, O, CH₃O—N, NHOH, H substituents on benzene ring]

where Z¹ represents the radicals specified in Table 1.

TABLE 57

(IB-11)

[Chemical structure showing pyrimidine compound with E, O, CH₃O—N, NHOH, H substituents]

where E represents the substituents specified in Table 2.

TABLE 58

(IC-11)

[Chemical structure showing thiadiazole compound with D, N, S, O, CH₃O—N, NHOH, H substituents]

where D represents the substituents specified in Table 3.

TABLE 59

(ID-11)

[Structure: benzene ring with ortho substituents; one side has CH₃−C(=N−O−)... with Z² attached; other side has C(=N−OCH₃)(N=CH−NHOH with H)]

where Z² represents the substituents specified in Table 4.

TABLE 60

(IE-11)

[Structure: benzene ring with ortho substituents; one side has CN−C(=N−O−) with Z² attached; other side has C(=N−OCH₃)(N=CH−NHOH with H)]

where Z² represents the substituents specified in Table 4.

The N,N-dialkyl-amidine derivatives which are required as starting compounds for carrying out the novel process are defined generally by the formula (II). In the formula (II), Ar, G, $R^1$, $R^2$, X, Z and m preferably or particularly preferably have those meanings which have already been mentioned above, in connection with the description of the compounds of the formula (I), as being preferred or particularly preferred for these substituents.

Alk preferably represents straight-chain or branched alkyl having from 1 to 4 carbon atoms, particularly preferably methyl or ethyl.

The N,N-dialkyl-amidine derivatives of the formula (II) are novel and are likewise a subject-matter of this invention. They are obtained when oxime derivatives of the formula (IV)

$$\underset{R^1O-N}{\overset{Z}{\diagdown}}\overset{Ar}{\underset{[X]_m}{\diagup}}NH_2 \quad (IV)$$

in which
Ar, G, $R^1$, X, Z and m have the abovementioned meaning, are reacted with aminal esters of the formula (Va) or amide acetals of the formula (Vb)

```
    OAlk'
    |
R²—C—NAlk₂           (Va)
    |
    NAlk₂
``` or

```
    OAlk'
    |
R²—C—OAlk'           (Vb)
    |
    NAlk₂
``` in which
Alk and $R^2$ have the abovementioned meaning, and
Alk' represents straight-chain or branched alkyl having from 1 to 4 carbon atoms, preferably methyl, ethyl, n- or i-propyl and n-, i-, s- or t-butyl, where appropriate in the presence of a diluent.

The oxime derivatives of the formula (IV) in which m=1 are known (cf., e.g. EP-A 0 398 692) or can be obtained, in a well known manner, using the methods described in that publication by, for example, reacting corresponding ester derivatives with ammonia (cf. the preparation examples as well).

The oxime derivatives of the formula (IV) in which m=0 are the subject-matter of a previous application of our own which has still not been disclosed (cf. German Patent Application P 44 08 006 of 10.03.1994). They are obtained by reacting corresponding keto derivatives of the formula (VI)

$$\underset{R^1O-HN}{\overset{Z}{\diagdown}}\overset{Ar}{\underset{O}{\diagup}} \quad (VI)$$

in which
Ar, G, $R^1$ and Z have the abovementioned meaning, with a sulphurizing agent, for example $P_4S_{10}$ or Lawesson's reagent, where appropriate in a diluent, for example xylene or toluene, at temperatures of between 80° and 200° C.; alkylating the resulting thione derivatives of the formula (VII)

$$\underset{R^1O-HN}{\overset{Z}{\diagdown}}\overset{Ar}{\underset{S}{\diagup}} \quad (VII)$$

in which
Ar, G, $R^1$ and Z have the abovementioned meaning, in a customary manner, for example with dimethyl sulphate or methyl iodide, and reacting the alkylated derivatives, obtained in this way, of the formula (VIII)

$$\underset{R^1O-N}{\overset{Z}{\diagdown}}\overset{Ar}{\underset{SCH_3}{\diagup}} \quad (VIII)$$

in which
Ar, G, $R^1$ and Z have the abovementioned meaning, in a customary manner using ammonia (cf. the preparation examples as well).

The aminal esters of the formula (Va) and the amide acetals of the formula (Vb) are compounds which are well known in organic chemistry.

Where appropriate, the reaction of the oxime derivatives of the formula (IV) with aminal esters of the formula (Va) or amide acetals of the formula (Vb) is carded out in the presence of a diluent. Dipolar, aprotic solvents, for example dimethylformamide, diethylformamide, N-methylformanilde and dimethylacetamide, are preferably used for this purpose.

When reacting the oxime derivatives of the formula (IV) with aminal esters of the formula (Va) or amide acetals of the formula (Vb), the reaction temperatures may be varied over a relatively wide range. In general, the reaction with aminal esters is carried out at temperatures of between 20° and 140° C, preferably at temperatures of between 20° and 40° C, while the reaction with amide acetals is carried out at between 100° and 130° C.

In order to carry out the reaction of the oxime derivatives of the formula (IV) with aminal esters of the formula (Va) or amide acetals of the formula (Vb), from 1 to 5 mol, preferably from 1 to 3 tool, of aminal ester of the formula (Va) or amide acetal of the formula (Vb) are generally employed per mole of oxime derivative of the formula (IV).

The hydroxylamine derivatives which are also required as starting compounds carrying out the novel process are defined generally by the formula (III). In the formula (III), $R^3$ preferably or particularly preferably has those meanings which have already been mentioned above, in connection with the description of the compounds of the formula (I), as being preferred or particularly preferred for this substituent.

The hydroxylamine derivatives of the formula (III) and also their acid addition salts, for example hydrochlorides and hydroacetates, are compounds which are well known in organic chemistry.

Inert organic solvents are suitable for use as diluents for carrying out the novel process. Those which may preferably be used are aliphatic, alicyclic or aromatic, optionally halogenated hydrocarbons, for example benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoramide, esters, such as ethyl acetate, or sulphoxides, such as dimethyl sulphoxide, alcohols, such as methanol or ethanol, or basic solvents, such as pyridine or triethylamine.

The novel process is preferably carried out in the presence of a suitable reaction auxiliary. All the inorganic and organic bases which may customarily be used are suitable for use as this auxiliary. Use if preferably made of alkali metal hydrides, hydroxides, alkoxides, acetates, carbonates or hydrogen carbonates, for example sodium hydroxide, sodium methoxide, sodium ethoxide, potassium t-butoxide, sodium acetate, potassium acetate, sodium carbonate, potassium carbonate or sodium hydrogen carbonate, or else tertiary amines, for example triethylamine, N,N-dimethylaniline, pyridine, N,N-dimethylaminopyridine, diazabicyclooctane (DABCO), diazabicyclononene (DBN) or diazabicycloundecene (DBU). Acid reaction auxiliaries, for example p-toluenesulphonic acid, are also advantageous, where appropriate.

When carrying out the novel process, the reaction temperatures may be varied over a relatively wide range. In general, the process is carried out at temperatures of between 0° C. and +130° C., preferably at temperatures of between 20° C. and 80° C.

In order to carry out the novel process, from 1 to 4 mol, preferably from 1 to 2 mol, of hydroxylamine derivative of the formula (III) and, where appropriate, from 1 to 3 mol, preferably from 1 to 2 mol, of reaction auxiliary are generally employed per mole of N-N-dialkyl-amidine derivative of the formula (II).

The implementation of the reaction, and the working-up and isolation of the reaction products, are effected using generally customary methods (cf. the preparation examples as well).

The novel active compounds of the formulae (I) and (II) exhibit a powerful microbicidal effect and may be employed in practice for controlling undesirable microorganisms. The active compounds are suitable for use as plant protectants, in particular as fungicides.

Fungicidal agents in plant protection are employed for controlling Plasmoiophoromycetes, Oomycetes, Chytridiomycetes, Zygomycetes, Ascomycetes, Basisdiomycetes and Deuteromycetes.

Some causative organisms of fungal diseases which come under the generic names listed above may be mentioned as examples, but not by way of limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, synonym: Helminthosporium);
Cochliobolus species, such as, for example, *Cochliobolus sativus* (conidia form: Drechslera, synonym: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septofia species, such as, for example, *Septofia nodorum;*
Leptosphaefia species, such as, for example, *Leptosphaeria nodorum;*
Cercospora species, such as, for example, *Cercospora canestens;*
Alternaria species, such as, for example, *Alternaria brassicae* and
Pseudocercosporella species, such as, for example, *Pseudocereosporella herpotrichoides.*

The good toleration, by plants, of the active compounds, at the concentrations required for controlling plant diseases, permits treatment of above-ground parts of plants, of vegetative propagation stock and seeds, and of the soil.

In this context, the novel active compounds may be employed particularly successfully for controlling diseases in fruit and vegetable cultivation, for example against Podosphaera species, for controlling cereal diseases, for example against Erysiphe, Leptosphearia, Pyrenophora and Fusarium species, or for controlling rice diseases, for example against *Pyricularia oryzae.*

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carders are meant liquids which are gaseous at ambient temperature and under atmospheric pressure, for example aerosol propellants, such as halogenated hydrocarbons as well as butane, propane, nitrogen and carbon dioxide; as solid carders there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carders for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or tatices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The novel active compounds are also used, as such or in their formulations, mixed together with known fungicides, bactericides, acaricides, nematicides or insecticides in order thereby, for example, to broaden the spectrum of activity or prevent the development of resistance. In many cases, synergistic effects appear under these circumstances. Examples of suitable compounds for the mixtures are
Fungicides 2-Aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)acetamide; 8-hydroxyquinoline sulphate; methyl-(E)-2-{2-[6-(2-cyanophenoxy)pyrimidin-4-yloxy]phenyl}-3-methoxyacrylate; methyl-(E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanide, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, teclofialam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram
Bactericides Bronopol, dichlorophen, nitrapyrin, nickel dimethyldithiocarbamate, kasugamycin, octhilinone, furan-carboxylic acid, oxytetracycline, probenazole, streptomycin, tecloftalam, copper sulphate and other copper preparations.
Insecticides/Acaricides/Nematicides Abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamdacyhalothfin, lufenuron, malathion, mecarbam, mervinphos, mesulfenphos, metaldehyde, methacrifos, methamidophos, methidathion, methiocarb, methomyl, metotcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyrachlophos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to have a mixture with other known active compounds, such as herbicides, or with fertilizers and growth regulators.

The active compounds can be used as such, in the form of their formulations or the use forms prepared therefrom, such as ready-to-use solutions, suspensions, wettable powders, pastes, soluble powders, dusting preparations and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of plants can also be treated.

In the treatment of parts of plants, the active compound concentrations in the use forms can be varied over a relatively wide range: they are, in general between 1 and 0.0001% by weight, preferably between 0.5 and 0.001% by weight.

In the treatment of seed, amounts of active compound of from 0.001 to 50 g per kilogram of seed, preferably from 0.01 to 10 g are generally required.

For the treatment of the soil, active compound concentrations of from 0.00001 to 0.1% by weight, preferably from 0.0001 to 0.02% by weight, are required at the site of action.

PREPARATION EXAMPLES

Example (I-1)

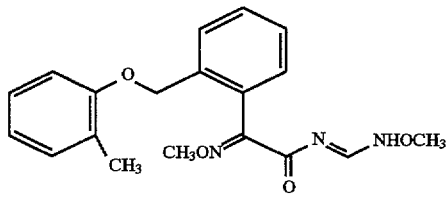

A mixture of 3.5 g (0.01 mol) of, -[2-(2-methylphenoxymethyl)-phenyl]-, -methoximino-N-(dimethylaminomethyliden)-acetamide(cf. Ex. II-1),1.0 g (0.012 mol) of O-methylhydroxylammonium chloride and 1.0 g (0.012 mol) of sodium acetate in 25 ml of methanol is stirred at room temperature for 24 hours. Following concentration, the residue is stirred up with ethyl acetate, and the organic phase is washed with water, dried over sodium sulphate and concentrated. The residue is purified chromatographically on silica gel (eluent: cyclohexane/ethyl acetate=2/1).

1.2 g (34% of theory) of, -[2-(2-methylphenoxymethyl)-phenyl]-,-methoximino-N-methoxyaminomethyliden)-acetamide are obtained.

$^1$HNMR (CDCl$_3$)/(ppm)=3.95 (s, 3H).

The compounds of the formula (I) which are listed in the following table are obtained in analogy with Example (I-1) and in conformity with the general description of the novel process:

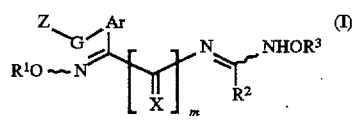

| Ex. No. | Z | G | Ar | X | m | R$^1$ | R$^2$ | R$^3$ | Physical Data |
|---------|---|---|----|----|---|------|------|------|---------------|
| I-2 | Cl-phenyl | —OCH$_2$— | phenyl-CH$_3$ | O | 1 | CH$_3$ | H | CH$_3$ | m.p. 86–88° C. |
| I-3 | CH$_3$-phenyl | —O—CH$_2$— | phenyl-CH$_3$ | O | 1 | CH$_3$ | H | H | m.p.: 106–107° C. |

-continued

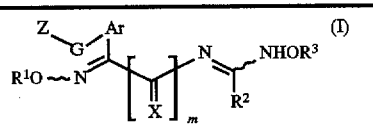

| Ex. No. | Z | G | Ar | X | m | R¹ | R² | R³ | Physical Data |
|---|---|---|---|---|---|---|---|---|---|
| I-4 | 2-methylphenyl | $-O-CH_2-$ | 1,2-phenylene | | 0 | $CH_3$ | H | $CH_3$ | NMR*): 3.9 (s, 3H) |
| I-5 | 2-methylphenyl | $-O-CH_2-$ | 1,2-phenylene | | 0 | $CH_3$ | H | H | NMR*): 3.85 (s, 3H) |
| I-6 | 2-methylphenyl | $-O-CH_2-$ | 1,2-phenylene | | 0 | $CH_3$ | H | $C_2H_5$ | NMR*): 3.9 (s, 3H) |
| I-7 | 3-CF₃-phenyl | $CH_3-C(=N-O-CH_3)-$ | 1,2-phenylene | O | 1 | $CH_3$ | H | $CH_3$ | NMR*): 4.05 (s, 3H) |
| I-8 | 3-CF₃-phenyl | $CH_3-C(=N-O-CH_3)-$ | 1,2-phenylene | O | 1 | $CH_3$ | H | H | NMR*): 4.05 (s, 3H) |
| I-9 | 3-CF₃-phenyl | $CH_3-C(=N-O-CH_3)-$ | 1,2-phenylene | O | 1 | $CH_3$ | H | $C_2H_5$ | NMR*): 4.05 (s, 3H) |
| I-10 | 2-methylphenyl | $-O-CH_2-$ | 1,2-phenylene | O | 1 | $CH_3$ | H | $C_2H_5$ | NMR*): 4.0 (s, 3H) |

*)The ¹H-NMR spectra were plotted in deuterochloroform ($CDCl_3$) or hexadeuterodimethyl sulphoxide (DMSO-$d_6$) using tetramethylsilane (TMS) as the internal standard. The chemical shift is given as the δ value in ppm.

Preparation of the starting compounds

Example (II-1)

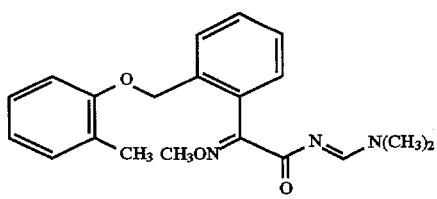

A mixture of 4.8 g (0.016 mol) of, -[2-(2-methylphenoxymethyl)-phenyl]-, -methoximino-acetamide and 6.6 g (0.038 mol) of tert-butoxy-bis(N,N-dimethylamino)methane (cf. Ex. IV-1) is stirred at 40° C. for 24 hours. After that, it is cooled down to room temperature and concentrated under high vacuum.

4.9 g (87% of theory) of, -[2-(2-methylphenoxymethyl)-phenyl]-,-methoximino-N-(dimethylaminomethylidene)-acetamide are obtained.

¹HNMR ($CDCl_3$)/(ppm)=4.0 (s, 3H).

Preparation of the precursor

Example (IV-1)

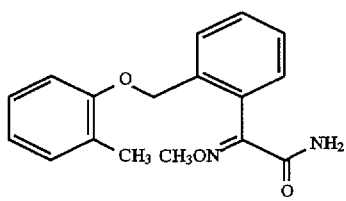

100 ml of a 25% aqueous solution of ammonia are added to 10 g (0.032 mol) of methyl 2-(2-methylphenoxymethyl)-,-methoximino-phenylacetate in 100 ml of methanol and the reaction mixture is heated under reflux for 5 hours. After that, a further 100 ml of a 25% aqueous solution of ammonia are added and the mixture is heated under reflux for a further 6 hours. A further 50 ml of a 25% solution of ammonia are added to complete the reaction and the reaction mixture is heated under reflux for 8 hours. After having been cooled down to room temperature, the reaction mixture is added to water and the whole is extracted with ethyl acetate, and the organic phase is washed with water, dried over sodium sulphate and concentrated in vacuo. The residue is stirred up with diisopropyl ether.

8.3 g (87% of theory) of, -[2-(2-methylphenoxymethyl)-phenyl]-,-methoximino-acetamide are obtained with a melting point of 93°–95° C.

Example (II-2)

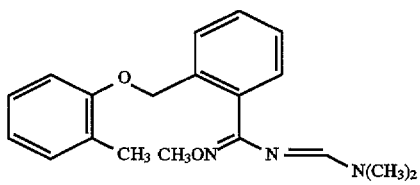

A mixture of 0.6 g (0.022 mol) of amino-methoximino-[2-(2-methylphenoxymethyl)-phenyl]-methane and 5 ml of tert-butoxy-bis (N,N-dimethylamino)-methane is stirred at room temperature overnight. The reaction mixture is then added to water, the whole is extracted with ethyl acetate, and the organic phase is washed with water, dried over sodium sulphate and concentrated.

0.6 g (83% of theory) of dimethylaminomethylidenamino-methoximino-[2-(2-methylphenoxymethyl)-phenyl]-methane is obtained.

$^1$HNMR (DMSO-d)/(ppm)=3.7 (s, 3H).

The precursors of the formula (II) which are listed in the following table are obtained in analogy with Examples (II-1) and (II-2) and in conformity with the general description:

| Ex. No. | Z | G | Ar | X | m | R$^1$ | Alk | Physical const |
|---|---|---|---|---|---|---|---|---|
| II-3 | 2-Cl-phenyl | —OCH$_2$— | 2-methylphenyl | O | 1 | CH$_3$ | CH$_3$ | m.p.112–114° C. |
| II-4 | 2,4-dimethylphenyl | —OCH$_2$— | 2-methylphenyl | O | 1 | CH$_3$ | CH$_3$ | 1HNMR*) 4.05(s, 3H) |
| II-5 | 2,5-dimethylphenyl | —OCH$_2$— | 2-methylphenyl | O | 1 | CH$_3$ | CH$_3$ | 1HNMR*) 4.05(s, 3H) |
| II-6 | 2,5-dimethylphenyl | C(CH$_3$)=N—O— | 2-methylphenyl | O | 1 | CH$_3$ | CH$_3$ | 1HNMR*) 4.0(s, 3H) |

*)The $^1$H—NMR spectra were plotted in deuterochloroform (CDCl$_3$) or hexadeuterodimethyl sulphoxide (DMSO-d$_6$) using tetramethylsilane (TMS) as the internal standard. The chemical shift is given as the δ value in ppm.

APPLICATION EXAMPLES

Example A

Erysiphe Test (wheat)/protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are dusted with spores of *Erysiphe graminis f.sp. tritici*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound according to Preparation Example (I-1) exhibits an efficacy of 100 at a rate of application of active compound of 250 g/ha.

Example B

Erysiphe Test (wheat)/curative

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.sp. tritici*. 48 Hours after the inoculation, the plants are sprayed with the preparation of active compound at the stated rate of application.

The plants are placed in a greenhouse at a temperature of about 20° C. and a relative atmospheric humidity of about 80% in order to promote the development of powdery mildew pustules.

Evaluation is carded out 7 days after the inoculation.

In this test, the compound according to Preparation Example (I-1 ) exhibits an efficacy of 100 at a rate of application of active compound of 250 g/ha.

Example C

Erysiphe Test (barley)/curative

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.sp. hordei*. 48 Hours after the inoculation, the plants are sprayed with the preparation of active compound at the stated rate of application.

The plants are placed in a greenhouse at a temperature of about 20° C. and a relative atmospheric humidity of about 80% in order to promote the development of powdery mildew pustules.

Evaluation is carried out 7 days after the inoculation.

In this test, the compound according to Preparation Example (I-I) exhibits an efficacy of 100 at a rate of application of active compound of 250 g/ha.

Example D

Podosphaera test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet.

After the spray coating has dried on, the plants are inoculated by dusting with conidia of the causative organism (*Podosphaera leucotricha*) of powdery mildew of apple.

The plants are then placed in a greenhouse at 23° C. and a relative atmospheric humidity of about 70%.

Evaluation is carried out 10 days after the inoculation.

In this test, the compound according to Preparation Example (I-1) exhibits an efficacy of 89% at an active compound concentration of 20 ppm.

Example E

Plasmopara test (vine)/protective

Solvent: 4.7 parts by weight of acetone

Emulsifier: 0.3 pans by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of *Plasmopara viticola* and then remain in a humidity chamber at 20° to 22° C. and 100% relative atmospheric humidity for 1 day. The plants are then placed in a greenhouse at 21° C. and 90% atmospheric humidity for 5 days. The plants are then moistened and placed in a humidity chamber for 1 day.

Evaluation is carried out 6 days after the inoculation.

The compound according to Preparation Example I-10 exhibits 84% efficacy at a rate of application of 100 ppm.

Example F

Podosphaera test (apple) (protective)

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated by dusting with conidia of the causative organism (*Podosphaera leucotricha*) of powdery mildew of apple.

The plants are then placed in a greenhouse at 23° C. and a relative atmospheric humidity of about 70%.

Evaluation is carried out 10 days after the inoculation.

The compounds according to Preparation Examples I-4, 1-52 and 1-53 exhibit up to 98% efficacy at an active compound concentration of 100 ppm.

Example G

Erysiphe Test (barley)/protective

Solvent: 10 parts by weight of N-methyl-pyrrolidone

Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application.

After the spray coating has dried on, the plants are dusted with spores of *Erysiphe graminis f.sp. hordei*.

The plants are placed in a greenhouse at a temperature of about 20° C. and a relative atmospheric humidity of about 80% in order to promote the development of powdery mildew pustules.

Evaluation is carried out 7 days after the inoculation.

The compounds according to Preparation Examples I-3 and II-6 exhibit a 100% efficacy at a rate of application of 250 g/ha.

Example H
Erysiphe Test (barley)/protective
Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application.

After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of powdery mildew pustules.

Evaluation is carried out 7 days after the inoculation.

The compound according to Preparation Example I-3 exhibits 100% efficacy at a rate of application of 250 g/ha.

Example I
Erysiphe Test (barley)/curative
Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. hordei. 48 Hours after the inoculation, the plants are sprayed with the preparation of active compound at the stated rate of application.

The plants are placed in a greenhouse at a temperature of about 20° C. and a relative atmospheric humidity of about 80% in order to promote the development of powdery mildew pustules.

Evaluation is carried out 7 days after the inoculation.

Compounds according to Preparation Example II-1 exhibits a 100% efficacy at a rate of application of 250 g/ha.

We claim:

1. N-Alkoxy-amidine derivatives of the general formula (I),

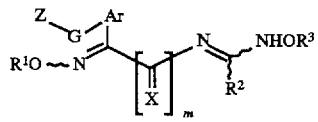

in which
Ar represents in each case optionally substituted arylene or heteroarylene;
G represents a single bond or oxygen, or represents alkanediyl, alkenediyl, oxaalkenediyl or alkinediyl which are in each case optionally substituted by halogen, hydroxyl, alkyl, halogenoalkyl or cycloalkyl, or represents one of the following groupings —Q—CQ—, —CQ—Q—, —CH$_2$—Q—;
—Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —CQ—CH$_2$— or —N=N—C(R$^4$)=N—O—, where
n represents the numbers 0, 1 or 2,
Q represents oxygen or sulphur,
R$^1$ represents hydrogen or alkyl;
R$^2$ represents hydrogen or alkyl;
R$^3$ represents hydrogen or alkyl;
R$^4$ represents hydrogen, cyano or in each case optionally substituted alkyl, alkoxy, alkylthio, alkylamino, dialkylamino or cycloalkyl, and
R$^5$ represents hydrogen, hydroxyl, cyano or in each case optionally substituted alkyl, alkoxy or cycloalkyl;
X represents oxygen or sulphur;
m represents the numbers 0 or 1, and
Z represents in each case optionally substituted alkyl, alkenyl, alkinyl, cycloalkyl, aryl or heterocyclyl.

2. Compounds of the formula (I) according to claim 1, in which represents in each case optionally substituted phenylene or naphthylene, or represents heteroarylene having 5 or 6 ring members of which at least one represents oxygen, sulphur or nitrogen and, with the substituents being selected from the following list:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case from 1 to 6 carbon atoms, in each case straight-chain or branched alkenyl, alkenyloxy or alkinyloxy having in each case from 2 to 6 carbon atoms, in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms, in each case straight-chain or branched halogenoalkenyl or halogenoalkenyloxy having in each case from 2 to 6 carbon atoms and from 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties, or in each case doubly linked alkylene or dioxyalkylene which in each case have from 1 to 6 carbon atoms and which are in each case optionally substituted identically or differently, once or more than once, by halogen and/or straight-chain or branched alkyl having from 1 to 4 carbon atoms and/or straight-chain or branched halogenoalkyl having from 1 to 4 carbon atoms and from 1 to 9 identical or different halogen atoms, G represents a single bond, or represents oxygen, or represents alkanediyl, alkenediyl, oxaalkenediyl or alkinediyl which in each case have up to 4 carbon atoms and which are in each case optionally substituted by halogen, hydroxyl, C$_1$–C$_4$-alkyl, C$_1$–C$_4$-halogenoalkyl or C$_3$–C$_6$-cycloalkyl, or represents one of the following groupings —Q—CQ—, —CQ—Q—, —CH$_2$—Q—;
—Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$)—CQ—Q—CH$_2$—, —CQ—CH$_2$— or —N=N—C(R$^4$)=N——, where n represents the numbers 0, 1 or 2, Q represents oxygen or sulphur, R$^4$ represents hydrogen or cyano, represents alkyl, alkoxy, alkylthio, alkylamino or dialkylamino which in each case have from 1 to 6 carbon atoms in the alkyl groups and which are optionally substituted by halogen, cyano or C$_1$–C$_4$-alkoxy, or represents cycloalkyl which has from 3 to 6 carbon atoms and which is in each case optionally substituted by halogen, cyano, carboxyl, C$_1$–C$_4$-alkyl or C$_1$–C$_4$-alkoxy-carbonyl, and R$^5$ represents hydrogen, hydroxyl or cyano, or represents alkyl which has from 1 to 6 carbon atoms and which is optionally substituted by halogen, cyano or C$_1$–C$_4$-alkoxy, or represents cycloalkyl which has from 3 to 6 carbon atoms and which is optionally substituted by halogen, cyano, carboxyl, C$_1$–C$_4$-alkyl or C$_1$–C$_4$-alkoxy-carbonyl, R$^1$ represents hydrogen or straight-chain or branched alkyl having from 1 to 4 carbon atoms, R$^2$ represents hydrogen or straight-chain or branched alkyl having from 1 to 4 carbon atoms, R$^3$ represents hydrogen or straight-chain or branched alkyl having from 1 to 4 carbon atoms, X represents oxygen or sulphur, m represents the numbers 0 or 1, and Z represents alkyl which has from 1 to 8 carbon atoms and which is optionally substituted by halogen, cyano, hydroxyl, amino, C$_1$–C$_4$-alkoxy, C$_1$–C$_4$-alkylthio, C$_1$–C$_4$-alkylsulphinyl or C$_1$–C$_4$-alkylsulphonyl (which are in each case optionally substituted by halogen), or represents alkenyl or alkinyl which in each case have up to 8 carbon atoms and which are in each case optionally substituted by halogen, represents cycloalkyl which has from 3 to 6 carbon atoms and which is in each case optionally substituted by halogen, cyano, carboxyl, phenyl (which is optionally substituted by halogen cyano, C$_1$–C$_4$-alkyl, C$_1$–C$_4$-halogenoalkyl, C$_1$–C$_4$-alkoxy or C$_1$–C$_4$-halogenoalkoxy), C$_1$–C$_4$-alkyl or C$_1$–C$_4$-alkoxycarbonyl, or represents in each case optionally substituted phenyl, naphthyl or (optionally benzofuzed) heterocyclyl having 5 or 6 ring members of which at least one represents oxygen, sulphur or nitrogen with the substituents being selected from the following list: oxygen (as a replacement for two geminate hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case from 1 to 6 carbon atoms, in each case straight-chain or branched alkenyl or alkenyloxy having in each case from 2 to 6 carbon atoms, in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms, in each case straight-chain or branched halogenoalkenyl or halogenoalkenyloxy having in each from 2 to 6 carbon atoms and from 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties, in each case doubly linked alkylene or dioxyalkylene which in each case have from 1 to 6 carbon atoms and which are in each case optionally substituted identically or differently, once or more than once, by halogen and/or straight-chain or branched alkyl having from 1 to 4 carbon atoms and/or straight-chain or branched halogenoalkyl having from 1 to 4 carbon atoms and from 1 to 9 identical or different halogen atoms, cycloalkyl having from 3 to 6 carbon atoms, heterocyclyl or heterocyclyl-methyl methyl having in each case from 3 to 7 ring members of which in each case from 1 to 3 are identical or different heteroatoms, in particular nitrogen, oxygen and/or sulphur, and also phenyl, phenoxy, benzyl, benzyloxy, phenylethyl or phenylethyloxy which are in each case optionally substituted identically or differently, once or more than once, in the phenyl moiety by halogen, cyano, nitro, carboxyl, carbamoyl and/or straight-chain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxy having from 1 to 4 carbon atoms and from 1 to 9 identical or different halogen atoms and/or alkylcarbonyl or alkoxycarbonyl having in each case up to 5 carbon atoms.

3. Compounds of the formula (I) according to claim 1, in which

Ar represents in each case optionally substituted ortho-, meta- or para-phenylene, or represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, with the substituents being selected, from the following list:

fluorine, chlorine, cyano, methyl, ethyl, trifluoromethyl, methoxy, ethoxy, methylthio, methylsulphinyl or methylsulphonyl, G represents a single bond, or represents oxygen, or represents methylene, dimethylene (ethane-1,2-diyl), etheneol,2-diyl or ethine-1,2-diyl, which are in each case optionally substituted by fluorine, chlorine, hydroxyl, methyl, ethyl, n- or i-propyl, trifluoromethyl, cyclopropyl, cyclobutyl, cyclopentyl or cyclohexyl, or represents one of the following groupings —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, CH$_2$—O—N=C(R$^4$)—, —N(R$^5$)—CQ—Q—, —CQ—N(R$^5$)—CQ—Q— or —N(R$^5$)—CQ—Q—CH$_2$—, where n represents the numbers 0, 1 or 2, Q represents oxygen or sulphur, R$^4$ represents hydrogen or cyano, or represents methyl, ethyl, n- or i-propyl, n-, i-, or s-butyl, methoxy, ethoxy, propoxy, butoxy, methylthio, ethylthio, propylthio, butylthio, methylamino, ethylamino, propylamino, dimethylamino or diethylamino which are optionally substituted by fluorine, chlorine, cyano, methoxy or ethoxy, or represents cyclopropyl, cyclobutyl, cyclopentyl or cyclohexyl which are in each case optionally substituted by fluorine, chlorine, cyano, carboxyl, methyl, ethyl, n- or i-propyl, methoxycarbonyl or ethoxycarbonyl, and R$^5$ represents hydrogen, hydroxyl or cyano, or represents methyl, ethyl, n- or i-propyl, n-, i-, s- or t-butyl which are in each case optionally substituted by fluorine, chlorine, cyano, methoxy or ethoxy, or represents cyclopropyl, cyclobutyl, cyclopentyl or cyclohexyl which are optionally substituted by fluorine, chlorine, cyano, carboxyl, methyl, ethyl, n- or i-propyl, methoxycarbonyl or ethoxy-carbonyl, R$^1$ represents hydrogen, methyl, ethyl, n- or i-propyl and also n-, i-, s- or t-butyl, R$^2$ represents hydrogen, methyl, ethyl, n- or i-propyl and also n-, i-, s- or t-butyl, R$^3$ represents hydrogen, methyl, ethyl, n- or i-propyl and also n-, i-, s- or t-butyl, X represents oxygen or sulphur, m represents the numbers 0 or 1, and Z represents methyl, ethyl, n- or i-propyl, n-, i-, s- or t-butyl which are optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (which are in each case optionally substituted by fluorine and/or chlorine), or represents allyl, crotonyl, 1-methyl-allyl, propargyl or 1-methyl-propargyl which are in each case optionally substituted by fluorine, chlorine or bromine, or represents cyclopropyl, cyclobutyl, cyclopentyl or cyclohexyl which are in each case optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzthiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, with the substituents being selected from the following list:

oxygen (as a replacement for two geminate hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or iopropoxy, methylthio, ethylthio, no or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl; trimethylene (propane- 1,3-diyl), methylenedioxy or ethylenedioxy, cyclopropyl, cyclobutyl, cyclopentyl or cyclohexyl which are in each case optionally substituted identically or differently, once or more than once, by fluorine, chlorine, methyl, ethyl, n- or i-propyl, and also phenyl, phenoxy, benzyl or benzyloxy which are in each case optionally substituted identically or differently, once or more than once, in the phenyl moiety by fluorine, chlorine, bromine, cyano, nitro, carboxyl, carbamoyl, methyl, ethyl, n- or i-propyl, n-, i-, s- or t-butyl, trifluoromethyl, methoxy, ethoxy, n- or i-propoxy, difluoromethoxy, trifluoromethoxy, acetyl, methoxycarbonyl or ethoxycarbonyl.

4. Compounds of the formula (I) according to claim 1, in which

Ar represents ortho-phenylene, pyridine-2,3-diyl or thiophene-2,3-diyl,

G represents oxygen, methylene or one of the following groupings

—CH$_2$—O—, —O—CH$_2$—, —S(O)$_n$—, —CH$_2$—S(O)$_n$—, —S(O)$_n$—CH$_2$—, —C(R$^4$)=N—O—, —O—N=C(R$^4$)—, —C(R$^4$)=N—O—CH$_2$—, —N(R$^5$)— or —CH$_2$—O—N=C(R$^4$)—, where n represents the numbers 0, 1 or 2, R$^4$ represents hydrogen, methyl or ethyl, and R$^5$ represents hydrogen, methyl or ethyl, R$^1$ represents methyl, R$^2$ represents hydrogen or methyl, R$^3$ represents hydrogen or methyl, X represents oxygen, m represents the numbers 0 or 1, and Z represents in each case optionally substituted phenyl, pyridinyl, pyrimidinyl, pyridazinyl, pyrazinyl, 1,2,3-triazinyl, 1,2,4-triazinyl or 1,3,5-triazinyl, with the substituents being selected from the following list:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoxyiminomethyl, ethoxyiminomethyl, methoxyiminoethyl, ethoxyiminoethyl, methylenedioxy or ethylenedioxy which are in each case optionally substituted identically or differently, once or more than once, by fluorine, chlorine, methyl or ethyl, and also phenyl, phenoxy, benzyl or benzyloxy which are in each case optionally substituted identically or differently, once or more than once, in the phenyl moiety by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

5. Process for preparing N-alkoxy-amidine derivatives of the general formula (I), characterized in that N-N-dialkyl-amidine derivatives of the formula (II)

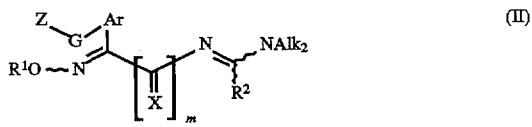

in which
AR, G, R¹, R², X, Z and m have the meaning given in claim 1, and
Alk represents alkyl,
are reacted with hydroxylamine derivatives of the general formula (III)

in which
R³ has the meaning given in claim 1,
or with their acid addition salts in the presence of a diluent and, where appropriate, in the presence of a reaction auxiliary.

6. N,N-Dialkyl-amidine derivatives of the formula (II)

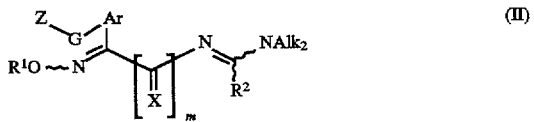

in which
Ar, G, R¹, R², X, Z and m have the meaning given in claim 1, and
Alk represents alkyl.

7. A pesticidal composition comprising a pesticidally effective amount of at least one compound of the formulae (I) or (II) according to claim 5.

8. A method of controlling pests, comprising applying to pests and/or their habitat a pesticidally effective amount of a compound of the formulae (I) or (II) according to claim 1.

9. Process for preparing pesticides, comprising mixing a compound of the formulae (I) or (II) according to claim 1 with extenders and/or surface-active agents.

10. Process for preparing N,N-dialkyl-amidine derivatives of the formula (II) according to claim 6, characterized in that oxime derivatives of the formula (IV)

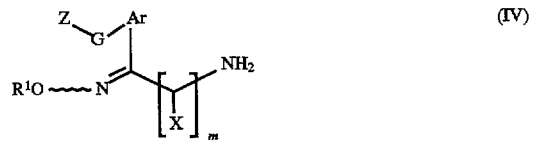

in which
Ar, G, R¹, X, Z and m have the meaning given in claim 6,
are reacted with aminal esters of the formula (Va) or amide acetals of the formula (Vb)

in which
Alk and R² have the meaning given in claim 6, and
Alk' represents straight-chain or branched alkyl having from 1 to 4 carbon atoms, preferably methyl, ethyl, n- or i-propyl and n-, i-, s- or t-butyl,
where appropriate in the presence of a diluent.

* * * * *

UNITED STATES PATENT AND TRADEMARK OFFICE
CERTIFICATE OF CORRECTION

PATENT NO. : 5,728,737
DATED : March 17, 1998
INVENTOR(S) : Heinemann, et al.

It is certified that error appears in the above-identified patent and that said Letters Patent is hereby corrected as shown below:

| | |
|---|---|
| Title Page & Col. 1 line 1 | Title [54]: After "DERIVATIVES" insert -- AND THEIR USE AS PESTICIDES --. |
| Col. 43, line 61 | Before " oxygen " delete " or " |
| Col. 44, line 29 | After " nitrogen " delete " and " |
| Col. 48, line 3 | Delete " iopropoxy " and substitute -- i-propoxy -- |
| Col. 50, line 3 | Delete claim " 5 " and substitute -- 1 -- |
| Col. 50, line 8 | After " claim 1 " insert -- are mixed -- |

Signed and Sealed this

Twenty-third Day of March, 1999

Attest:

Q. TODD DICKINSON

*Attesting Officer*  *Acting Commissioner of Patents and Trademarks*